United States Patent [19]

Karmiol et al.

[11] 4,443,601

[45] Apr. 17, 1984

[54] RECOVERY OF CAFFEINE FROM CAFFEINE ADSORBENTS

[75] Inventors: Mark H. Karmiol, Warwick; Gary L. Hickernell, Ossining; Bertrand J. Hall, Pearl River, all of N.Y.

[73] Assignee: General Foods Corporation, White Plains, N.Y.

[21] Appl. No.: 420,158

[22] Filed: Sep. 20, 1982

[51] Int. Cl.$^3$ ............................................ C07D 239/96
[52] U.S. Cl. .................................... 544/274; 544/275
[58] Field of Search ............................... 544/274, 275

[56] References Cited

U.S. PATENT DOCUMENTS 2,472,881 6/1949 Bender.
4,298,736 11/1981 Katz et al. ........................... 544/275

FOREIGN PATENT DOCUMENTS 1532547 11/1978 United Kingdom.

Primary Examiner—Nicholas S. Rizzo
Attorney, Agent, or Firm—R. L. Crisona; T. V. Sullivan; T. R. Savoie

[57] ABSTRACT

Caffeine adsorbed on caffeine adsorbents is recovered by contacting the carbon with a solvent, preferably an aqueous solution of ethylene carbonate or propylene carbonate. The caffeine adsorbent is contacted with the solvent for a period time sufficient to remove at least a portion of the caffeine adsorbed thereon and then separated from caffeine-containing solvent. The caffeine may be recovered from the solvent by precipitation.

11 Claims, No Drawings

RECOVERY OF CAFFEINE FROM CAFFEINE ADSORBENTS

TECHNICAL FIELD

The present invention relates to the removal of caffeine adsorbed on caffeine adsorbents. More particularly, the invention involves contacting an adsorbent containing adsorbed caffeine with a solvent comprising ethylene carbonate or propylene carbonate. The adsorbent is contacted with the solvent for a period of time sufficient to remove at least a portion of the caffeine and then separated from caffeine-containing solvent. Caffeine may then be recovered from the solvent.

BACKGROUND ART

The decaffeination of a vegetable material, such as aqueous coffee extract, is an important commercial process receiving much industry attention. One decaffeination approach of increasing interest is the use of caffeine adsorbents such as activated carbon or polymeric resins to adsorb caffeine from an extract. The adsorbents have not enjoyed wide acceptance though because of their tendency to adsorb large amounts of no-caffeine solids along with caffeine. In order to reduce the amount of non-caffeine solids adsorbed, the adsorbent may be treated with a mixture of carbohydrates prior to decaffeination, as is known in the art. After decaffeination of coffee extract, the adsorbent has caffeine, a small amount of non-caffeine coffee solids and carbohydrates adsorbed thereon.

Methods of recovering the adsorbed solids and caffeine are disclosed in U.S. Pat. No. 4,298,736 to Katz et al. and commonly assigned U.S. Pat. App. Ser. No. 488,354 of Katz et al. According to the Katz et al. patent, spent adsorbent is contacted with an organic acid or alcohol so that essentially all of the solids contained on the adsorbent are removed. The Katz et al. patent application describes the use of an aqueous acetic acid solution to achieve the same result. After the removal of the solids, the desorbent acid or alcohol is steam stripped and recovered from solution, leaving a caffeine-containing decaffienation process sludge. While the Katz et al. processes are effective in removing the solids and caffeine adsorbed on the adsorbent, both processes use organic acids, which acids may pose special handling problems.

It is an object of the present invention to provide a process for recovering caffeine adsorbed on activated carbon which process uses a solvent that does not pose any special handling problems.

DISCLOSURE OF THE INVENTION

It has now been discovered that the objects of the invention are met by a process involving contacting a caffeine adsorbent containing adsorbed caffeine with a solvent comprising ethylene carbonate or propylene carbonate. Contact of the adsorbent and the solvent is maintained for period of time sufficient to remove at least a portion of the caffeine from the adsorbent into the solvent. The caffeine adsorbent is subsequently separated from the caffeine-containing solvent and the caffeine may then be recovered from the solvent.

The specific solvents contemplated for use in this invention comprise ethylene carbonate, propylene carbonate or a mixture of the two, preferably in an aqueous solution. Said solvents are relatively high-boiling, non-flammable liquids. Significantly, ethylene carbonate and propylene carbonate are non-toxic. The non-toxic nature of the solvents is important because the caffeine eventually recovered therefrom has commerical food and pharmaceutical uses. Additionally, ethylene carbonate and propylene carbonate are relatively inexpensive and commercially available.

Specific caffeine adsorbents intended for use in the invention include activated carbon and polymeric resins. Decaffeination of a coffee extract with activated carbon is known in the art. Spent carbon, carbon that has adsorbed its limit of caffeine, generated by the processes known in the art is ideally suited to treatment by the present invention. The use of polymeric resins in decaffeinating aqueous coffee extracts is described in U.S. Pat. No. 4,113,887 to Kramer et al., as well as U.S. Pat. No. 4,113,888 to Henig et al. Decaffeination of a coffee extract with treated polymeric resins, particularly resins of the non-ionogenic, macroreticular, cross-linked type is also disclosed in commonly assigned U.S. Pat. App. Ser. No. 363,712 of Katz. The process of the present invention is similarly well suited to removing caffeine from spent resin generated by the resin processes.

An aqueous solution of either solvent is preferred because said aqueous solution has greater caffeine capacity than pure ethylene carbonate or propylene carbonate. It has been found that an ethylene carbonate or propylene carbonate concentration of 20% by weight or greater in aqueous solution works well. The optimal ethylene carbonate or propylene carbonate concentrations in solution are determined by two competing factors. First, the specificity of the solvents for caffeine, that is the solvents' tendency to desorb adsorbed caffeine in preference to any adsorbed solids, increases with increasing ethylene carbonate or propylene carbonate concentration. The other competing factor is the caffeine capacity of the solvent which decreases with increasing ethylene carbonate concentration.

Contact of the caffeine adsorbent containing adsorbed caffeine with the solvent may be in any vessel providing good solid-liquid contact. For example, said adsorbent and solvent may be contacted batch-wise in slurry fashion or alternatively may be contacted in a counter-current extraction battery. So too, the adsorbent may be contacted with ethylene carbonate or propylene carbonate in a continuous pulsed column arrangement. In any event, contact should be maintained for period of time sufficient to remove at least a portion of the caffeine adsorbed on the caffeine adsorbent into the solvent. Preferably, contact is maintained long enough to recover at least 50% by weight of the caffeine adsorbed on the adsorbent.

The temperature at which the adsorbent is contacted with the solvent may vary over a wide range. However, the caffeine capacity of the ethylene carbonate or propylene carbonate solvent increases with increasing temperature and it is preferable to use a temperature greater than ambient. Contact of the carbon and the ethylene carbonate or propylene carbonate at a temperature between 20° C. and 100° C. is convenient because no special pressure vessels are required at such a pressure. Preferably though, contact is at a temperature between 100° C. and 200° C. which higher temperature aids caffeine removal. The use of such a high temperature does not pose any problems because ethylene carbonate and propylene carbonate are both relatively high boiling.

Once the solvent and caffeine adsorbent have been contacted for a sufficient period time, the relatively caffeine-free adsorbent may be separated from the caffeine-containing ethylene carbonate or propylene carbonate solvent. The adsorbent may then be reactivated as by thermal reactivation in the case of activated carbon and subsequently returned to a decaffeination process. Preferably though, a sufficient amount of caffeine has been removed from the adsorbent so that said adsorbent may be used in the decaffeination process one or more times prior to reactivation. In view of the high cost of reactivation, such additional use prior to reactivation represents a great economic savings for the present invention.

Caffeine may be recovered from the solvent by precipitation. A concentrated salt solution, such as 50% by weight aqueous potassium carbonate or 40% by weight aqueous ammonium sulfate, is added to the caffeine-containing solvent. The salt solution is added at a weight ratio of about 1:1 salt solution to caffeine-containing ethylene carbonate and propylene carbonate. The salt alters the polarity of the caffeine-containing solution causing the caffeine to precipitate therefrom. The caffeine so precipitated may then be recovered by filtration or centrifugation.

The relatively caffeine-free ethylene carbonate or propylene carbonate may then be recycled to the process for contact with additional caffeine-containing adsorbent. Water is first removed from the relatively caffeine-free ethylene carbonate or propylene carbonate by boiling, which boiling also removes the salt from the solvent. The solvent is then diluted to the desired concentration and recycled. Any non-caffeine solids remaining in the solvent from the initial cycle may be left in the solvent during subsequent cycles. Eventually, said solvent should become saturated with the non-caffeine solids which should limit the amount of said solids removed in subsequent cycles thereby improving the specificity of the ethylene carbonate or propylene carbonate solvent.

The following examples are intended to illustrate more fully certain embodiments of the present invention. The examples are not intended to limit the invention beyond which is claimed below.

EXAMPLE 1

1. 50 gm of spent activated carbon derived from the operation of an activated carbon decaffeination process was loosely packed into a jacketed glass column 20 cm in length by 3 cm in diameter. The decaffeination method comprised first adsorbing carbohydrates on the carbon and subsequently contacting the carbon with a caffeine-containing green coffee extract in a counter-current multi-stage extraction battery. The activated carbon had approximately 20% by weight total solids (coffee solids, caffeine and carbohydrate solids) adsorbed thereon, of which about 50% by weight of the carbon was adsorbed caffeine.

2. A 20% by weight aqueous solution of ethylene carbonate was passed through the column at a rate of 5 ml/min and at a temperature between 70° C. and 80° C. for a period of about 20 minutes. The effluent caffeine-containing ethylene carbonate was collected for later analysis.

3. The carbon was subsequently rinsed with water and then dried in an oven. The carbon was found to have lost about 15% of its original weight indicating removal of about 75% of the solids initially present.

The effluent ethylene carbonate was analyzed and found to contain about 70% of the caffeine initially adsorbed on the carbon.

EXAMPLE 2

Ethylene carbonate containing caffeine, non-caffeine coffee solids and carbohydrates as in Example 1 was mixed with a solution of 50% by weight potassium carbonate. The ethylene carbonate was mixed with the salt solution at a weight ratio of 1:1. Caffeine was precipitated from solution and recovered by filtration.

A second sample of ethylene carbonate containing the same as above was mixed with a solution of 40% by weight ammonium sulfate. The ethylene carbonate was mixed with the salt solution at a weight ratio of 1:1. Caffeine was precipitated from solution and recovered by filtration.

What is claimed is:

1. A process for recovering caffeine adsorbed on a caffeine adsorbent which comprises:
   (a) contacting a caffeine adsorbent having at least caffeine adsorbed thereon with a solvent selected from the group consisting of ethylene carbonate, propylene carbonate, aqueous solution of ethylene carbonate or propylene carbonate and any combination thereof;
   (b) maintaining the contact between the caffeine adsorbent and the solvent at a temperature between 20° C. and 200° C. until at least a portion of the coffee adsorbed on the adsorbent is removed into said solvent;
   (c) subsequently separating the caffeine adsorbent from the caffeine-containing solvent.

2. The process of claim 1 wherein the solvent is an aqueous solution comprising 20% by weight or greater ethylene carbonate.

3. The process of claim 1 wherein the solvent is an aqueous solution comprising 20% by weight or greater propylene carbonate.

4. The process of claim 2 or 3 wherein the caffeine adsorbent is activated carbon.

5. The process of claim 2 or 3 wherein the caffeine adsorbent is a macroreticular, non-ionogenic, cross-linked polymeric resin.

6. The process of claim 1 wherein the contact is maintained at a pressure of about atmospheric.

7. The process of claim 1 wherein the contact is maintained at a pressure in excess of atmospheric.

8. The process of claim 1 wherein the contact is maintained for a period of time sufficient to remove at least 50% by weight of the caffeine from the caffeine adsorbent and into the solvent.

9. The process of claim 8 which further comprises recovering the caffeine from the solvent by adding a concentrated aqueous salt solution to said solvent thereby precipitating caffeine and filtering the precipitated caffeine from the solvent.

10. The process of claim 9 wherein the aqueous salt solution comprises potassium carbonate.

11. The process of claim 9 wherein the aqueous salt solution comprises ammonium sulfate.

* * * * *

UNITED STATES PATENT AND TRADEMARK OFFICE
CERTIFICATE OF CORRECTION

PATENT NO. : 4,443,601
DATED : Apr. 17, 1984
INVENTOR(S) : Mark H. Karmiol et al.

It is certified that error appears in the above-identified patent and that said Letters Patent are hereby corrected as shown below:

Col 3 line 59 delete "50" and insert --5--

Col 4 line 34 delete "coffee." and insert --caffeine--

Signed and Sealed this

Twenty-eighth Day of August 1984

[SEAL]

Attest:

GERALD J. MOSSINGHOFF

Attesting Officer

Commissioner of Patents and Trademarks